United States Patent [19]

Bardsley et al.

[11] Patent Number: 5,955,479

[45] Date of Patent: *Sep. 21, 1999

[54] LEVOBUPIVACAINE FOR MANAGING CHRONIC PAIN

[75] Inventors: Hazel Judith Bardsley, Cambridge, United Kingdom; Laurence Mather, Sidney, Australia

[73] Assignee: Darwin Discovery Ltd., United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/628,689

[22] PCT Filed: Oct. 13, 1994

[86] PCT No.: PCT/GB94/02248

§ 371 Date: Jul. 22, 1996

§ 102(e) Date: Jul. 22, 1996

[87] PCT Pub. No.: WO95/10276

PCT Pub. Date: Apr. 20, 1995

[30] Foreign Application Priority Data

Oct. 13, 1993 [GB] United Kingdom .................... 9321061

[51] Int. Cl.⁶ .................................................. A61K 31/445
[52] U.S. Cl. ............................................................ 514/330
[58] Field of Search .............................................. 514/330

[56] References Cited

U.S. PATENT DOCUMENTS 4,695,576  9/1987  Ekenstam et al. .

FOREIGN PATENT DOCUMENTS 6802611  12/1968  South Africa .

OTHER PUBLICATIONS

Clark et al., J. Chromatography. 553(1–2), 383–90 (1991).
Valenzuela, C. et al. (1994) "Stereoselective Bupivacaine Block of the Human Cardiac Delayed Rectifier Kv1.5 Channel" Biophys. J. 66:A205, abstract no. Tu–Pos383.
Butterworth, J.F. et al. (1993) "Bupivacaine Inhibits Cyclic–3', 5'–Adenosine Monophosphate Production" Anesthesiology 79:88–95.
Clarkson, C.W., L.M. Hondeghem (1985) "Mechanism for Bupivacaine Depression of Cardiac Conduction: Fast Block of Sodium Channels during the Action Potential with Slow Recovery from Block during Diastole" Anesthesiology 62:396–405.
Courtney, K.R., J.J. Kendig (1988) "Bupivacaine is an effective potassium channel blocker in heart" Biochimica et Biophysica Acta 939:163–166.
Burm, A.G.L. et al. (1994) "Pharmacokinetics of the enantiomers of bupivacaine following intravenous administration of the racemate" Br. J. Clin. Pharmac. 38:125–129.
Vanhoutte et al. (1991) "Steroselective effects of the enantiomers of bupivacaine on the electrophysiological properties of the guinea–pig papillary muscle" BR. J. PHARMACOL. 103(1):1275–1281.

Denson et al. (1992) "Enantiomer–Specific Effects of an Intravenously Adminstered Arrhythogenic Dose of Bupivacaine on Neurons of the Nucleus Tractus Solitarius and the Cardiovascular System in the Anesthetized Rat" REG. ANESTH. 17(6):311–316.
Rutten et al. (1991) "Cardiovascular Effects And Regional Clearances of I.V. Bupivacaine In Sheep: Enantiomers Analysis" BR. J. ANAESTH 67(3)247–256.
Aberg, G. (1972) "Toxicological and Local Anaesthetic Effects of Optically Active Isomers of Two Local Anaesthetic Compounds" Acta Pharmacol. Toxicol. 31(4):273–286.
Luduena, F. P. et al. (1972) "Optical Isomers of Mepivacaine and Bupivaine" Arch. Int. Pharmacodyn. Ther. 200(2):359–369.
Rutten, A.J. et al. (1993) "Tissue Distribution of Bupivacaine Enantiomers in Sheep" Chirality 5(7):485–491.
Maziot, J.X. et al. (1993) "Myocardial Uptake of Bupivacaine: II. Pharmacokinetics and Pharmacodynamics of Bupivacaine Enantiomers in the Isolated Perfused Rabbit Hearts" Anesth. Analg. 77(3):477–482.
Lee–Son, S. et al. (1992) "Stereoselective Inhibition of Neuronal Sodium Channels by Local Anesthetics" Anesthesiology 77(2):324–335.
Wang, G.K. et al. (1992) "Altered Stereoselectivity of Cocaine and Bupivacaine Isomers in Normal and Batrachotoxin–modified Na+ Channels" J. Gen. Physiol. 100(6):1003–1020.
Aps, C. et al. (1978) "An Intradermal Study Of The Local Anaesthetic And Vascular Effects Of The Isomers Of Bupivacaine" BR. J. Clin. Pharmacol. 6(1):63–68.
Chemical Abstracts 73(5):25314a, (1970).
Rutten, A.J. et al. (1992) "Postoperative course of plasma protein binding of lignocaine, ropivacaine and bupivacaine in sheep" J. Pharm. Pharmacol. 44(4):355–358.
Gristwood, R. et al. (1994) Reduced cardiotoxicity of levobupivacaine compared with racemic bupivacaine (Marcaine): new clinical evidence: Expert Opin. Invest. Drugs 3(11):1209–1212.
Ariens, E.J. (1990) "Stereoselectivity in pharmacodynamics and pharmacokinetics" Schweiz. Med. Wochenschr. 120(5):131–134.
Ariens, E.J. (1991) "Racemic therapeutics—ethical and regulatory aspects" Eur. J. Clin. Pharmacol. 41(2):89–93.
Testa, B. et al. (1990) "Racemates Versus Enantiomers in Drug Development: Dogmatism or Pragmatism?" Chirality 2:129–133.

*Primary Examiner*—Phyllis G. Spivaek
*Attorney, Agent, or Firm*—Saliwanchik, Lloyd & Saliwanchik

[57] ABSTRACT

The present invention concerns the use of levobupivacaine for the treatment of chronic pain in a patient. Levobupivacaine used in the subject methods is substantially free of dexbupivacaine. The methods of the invention can be used, for example, to treat pain in patients that are cardiac compromised, suffering from central nervous system damage or cancer.

9 Claims, No Drawings

LEVOBUPIVACAINE FOR MANAGING CHRONIC PAIN

This application is a 371 of PCT/GB94/02248 filed Oct. 13, 1994.

FIELD OF THE INVENTION

This invention relates to a new therapeutic use for a known analgesic agent, i.e. bupivacaine or 1-butyl-N-(2,6-dimethylphenyl)-2-piperidinecarboxamide.

BACKGROUND OF THE INVENTION

Racemic bupivacaine, a long-acting local anaesthetic, is useful in chronic administration as an analgesic in some pain syndromes. However, racemic bupivacaine is cardiotoxic, having depressant electrophysiological and mechanical effects on the heart. It should therefore be used with caution in cardiac-compromised patients.

It is known that levobupivacaine is probably less cardiotoxic than dexbupivacaine and racemic bupivacaine. See, for example, Vanhoutte et al, Br. J. Pharmacol. 103:1275–1281 (1991), and Denson et al, Regional Anaesthesia, 17:311–316 (1992). Vanhoutte et al studied the effects of bupivacaine enantiomers on the electrophysiological properties of guinea pig isolated papillary muscle; this is based on their statement that "the cardiotoxicity of bupivacaine seems to be mainly of electrophysiological origin".

Berrisford et al, Br. J. Anaesthesia 70:201–204 (1993), disclose the administration of bupivacaine and its enantiomers during continuous extrapleural intercostal nerve block, as an analgesic for patients who have undergone thoracotomy. The infusion of bupivacaine was maintained until the morning of the fifth day after operation.

Du Pen et al, Pain 49:293–300 (1992), report the use of chronic epidural and opioid infusions in concentrations between 0.1 and 0.5% bupivacaine in intractable cancer pain. The median length of therapy was 60–120 days, with the longest infusion lasting 277 days. A progressive reduction in bupivacaine clearance was reported.

Cardiotoxicity is not usually a clinical problem at low single doses, e.g. by use in epidurals and nerve blockade. However, for chronic administration, the myocardium may have to withstand the possible cumulative cardiotoxic side-effects of the local anaesthetic.

Pain has been classified, by the WHO Analgesic Ladder; see also the review by Ashburn and Lipman, "Management of Pain in the Cancer Patient". At the first step of the ladder, of mild to moderate pain, treatment with a non-opioid±adjuvant is required. If pain persists. or increases, treatment should be with an opioid for mild to moderate pain, plus non-opioid±adjuvant. If pain persists or increases beyond this second step, an opioid for moderate to severe pain is required, with or without non-opioid and/or adjuvant. Cancer and post-operative pain is typically of this third step.

An individual can be at any step on this ladder of pain at any time. Patents with acute pain will tend to go down the ladder with time; patients with chronic pain or malignancy may "climb the ladder" with time, increasingly potent analgesics then being required to control the worsening pain associated with progression of the disease.

SUMMARY OF THE INVENTION

It has now been found that there is less tissue uptake of levobupivacaine into ventricle and brain than dexbupivacaine. Levobupivacaine thus exhibits improved clearance. This, coupled with the evidence that levobupivacaine is less cardiotoxic than dexbupivacaine, supports the use of levobupivacaine as an improved, practical long-acting analgesic, i.e. for use in chronic pain management. This finding may be particularly beneficial for, but is not restricted to, human patients with compromised cardiac function and central nervous system damage or those predisposed to these conditions. In particular, cancer patients are a group likely to benefit from this agent.

The agent may be the single isomer, but is effectively free of dexbupivacaine, e.g. in at least 80%, more preferably at least 90%, and most preferably at least 99%, enantiomeric excess. Any conventional salt, e.g. the hydrochloride, may be used.

DESCRIPTION OF THE INVENTION

For the purposes of the present invention, the management of chronic pain involves administration of levobupivacaine for a period of at least 2 days, preferably at least 30 days, e.g. up to 60 days or more. As indicated above, the chronic pain may be associated with cancer. Other suitable subjects are those suffering from post-operative pain, or from severe pain caused by other chronic medical conditions.

In use of the invention, levobupivacaine may be provided in solution, for administration by infusion. This may be done using conventional apparatus, e.g. including means for the patient to induce infusion as desired. concentration of levobupivacaine to be given for effective utility, is for example, 0.25%, 0.5% or 0.75%, depending on the procedure envisaged. Up to 60 ml in a single dose can be given. The usual routes of administration are infiltration, epidural, spinal and peripheral nerve block. It is also possible to provide continuous infusion of agent at lower concentration, for example 0.125%, with or without opioid, depending on anaesthetic practice.

Administration of the active agent may be directly into the spine or epidural space. The agent is thus provided in the desired locus. By contrast with a conventional drug that is required to pass the blood-brain barrier, active agent acts, and then passes into the blood, for clearance. Accumulation is to be avoided; the present invention relies on the known activity of bupivacaine and the surprising discovery that levobupivacaine does not accumulate in the heart and brain as much as the other component (dexbupivacaine) of racemic bupivacaine. Clinicians can thus utilise the present invention without the likelihood of incurring long-term problems associated with the dexbupivacaine content of racemic bupivacaine. The treatment of the present invention, i.e. to mitigate the effect of chronic pain, is to be distinguished from the use of bupivacaine as a local anaesthetic, i.e. to avoid the effect of induced pain.

The term "chronic pain" is used herein to indicate a longer pain state than is currently associated with the use of racemic bupivacaine as a local anaesthetic. Thus the invention includes the treatment of patients who are suffering from what a skilled clinician might call "acute pain". The reduced toxicity risk associated with the use of levobupivacaine justifies both long-term administration and the use of higher concentrations, leading to a significant therapeutic benefit.

Categories of pain are given in Table 1.

TABLE 1

| Pain Type | Acute | Chronic (non-malignant) | Chronic (malignant) |
|---|---|---|---|
| Duration | Hours to days | Months to years | Unpredictable |
| Associated pathology | Present | Often none | Usually present |
| Prognosis | Predictable | Unpredictable | Increasing pain with possibility of disfigurement and fear of dying |
| Associated problems | Uncommon | Depression, anxiety | Many, especially fear |
| Nerve conduction | Rapid | Slow | Slow |
| Autonomic nervous system | Present | Generally absent | Present or absent |
| Biological social effects | High minimal | Low or absent | Variable, usually marked |
| Treatment | Primary analgesics | Multimodal: often largely behavioural, drugs play a minor role | Multimodal: drugs usually play a major role |

Levobupivacaine may be effectively used as an adjuvant to opioids in the treatment of severe pain for the following reasons:

1) Breakthrough pain is possible despite the use of opioids, and neuropathic pain affecting the central or afferent nerve ways often responds poorly to these agents.
2) Most cancer patients have pain of more than one aetiology and each must be treated separately.
3) In the treatment of advanced pain, drugs such as morphine have a ceiling effect above which additional analgesia does not occur but side-effects increase and tolerance is sometimes seen.
4) Although most patients are treated by the oral route, 60% will require drug administration by additional or alternative routes during the last four weeks of life. The use of levobupivacaine in post-operative pain control may be a simpler proposition. Bupivacaine has been demonstrated to be effective in the control of post-operative pain, and to reduce the opioid requirements of patients recovering from herniorrhaphy. In this study, the surgical wound was infiltrated with anaesthetic before closure. A low concentration of 0.25% was used; with levobupivacaine, higher levels could result in improved clinical benefit.

The evidence for the selective tissue uptake is as follows:

Four sheep weighing 39–49 kg (mean 44, SD 4 kg) were given increasing bolus doses (from 40 mg) of racbupivacaine HCl These were administered at least 1 day apart via a PVC cannula until a fatal outcome resulted. The heart and brain were removed within 20 min of death to be analysed for bupivacaine concentration. The heart was removed by transection through the great vessels approximately 20 mm above the level of the aortic valve, and 20 mm below the caudal border of the right atrium. Blood was immediately expressed from the cardiac chambers, and representative samples of the left and right atrium and ventricle were obtained, blotted and stored frozen (−20° C.) until assay. The brain was removed by transection at the level of the lower border of the pons, blotted and stored frozen as for the heart tissue.

Tissue concentrations of the bupivacaine enantiomers are presented in Table 2. The variability in the fatal doses (80–200 mg) was reflected in the tissue concentrations measured post-mortem. Larger differences in the concentrations of both bupivacaine enantiomers in the atrium and ventricle were apparent. Significant differences in the concentrations of the bupivacaine enantiomers in the ventricle and brain (both P=0.03 by the Students paired t test) were evident, more (+)-(R)- than (−)-(S)-bupivacaine being taken up by these tissues. This was not so for the atrium.

TABLE 2

| Sheep No. | Fatal dose (mg) | Enantiomer | Tissue concentration (μg/g) | | |
|---|---|---|---|---|---|
| | | | Atrium | Ventricle | Brain |
| 1 | 80 | R- | 5.70 | 9.93 | 6.91 |
| | | S- | 6.22 | 8.44 | 6.53 |
| | | R:S | 0.92 | 1.18 | 1.06 |
| 2 | 80 | R- | 3.94 | 7.70 | 4.97 |
| | | S- | 3.65 | 7.36 | 4.59 |
| | | R:S | 1.08 | 1.05 | 1.08 |
| 3 | 200 | R- | 17.9 | 45.6 | 12.7 |
| | | S- | 18.0 | 44.1 | 11.7 |
| | | R:S | 0.99 | 1.03 | 1.09 |
| 4 | 200 | R- | 21.5 | 34.1 | 17.2 |
| | | S- | 21.2 | 33.3 | 16.3 |
| | | R:S | 1.02 | 1.03 | 1.08 |

An additional benefit of levobupivacaine over racemic bupivacaine is its reduced cardiodepressant effect. It is therefore particularly suitable for use in treated cardiac-compromised patients. This is described more fully in published International Patent Application No. PCT/GB94/02249, filed Oct. 13, 1994.

We claim:

1. A method for treating chronic pain in a human patient, said method comprising administration of an effective amount of levobupivacaine or a salt thereof, to said patient, wherein said levobupivacaine is substantially free of dexbupivacaine.
2. The method, according to claim 1, wherein the patient has cancer.
3. The method, according to claim 1, wherein the patient is concomitantly treated with an opioid.
4. The method, according to claim 1, wherein the patient is cardiac-compromised.
5. The method, according to claim 1, wherein the pain is of more than 2 days duration.
6. The method, according to claim 5, wherein the duration is at least 30 days.
7. The method, according to claim 5, wherein the duration is at least 60 days.
8. The method, according to claim 1, wherein the levobupivacaine is in at least 90% enantiomeric excess with respect to dexbupivacaine.
9. The method, according to claim 1, wherein said pain is post-operative pain.

* * * * *